US00PP37617P2

(12) United States Plant Patent
de Boer

(10) Patent No.: US PP37,617 P2
(45) Date of Patent: Aug. 18, 2026

(54) ***NEPHROLEPIS* PLANT NAMED 'DEBO2025'**

(50) Latin Name: *Nephrolepis exaltata*
Varietal Denomination: DEBO2025

(71) Applicant: Debo-Plant, Asten (NL)

(72) Inventor: Hein Johannes Petrus de Boer, Asten (NL)

(73) Assignee: Debo-Plant, Asten (NL)

( * ) Notice: Subject to any disclaimer, the term of this patent is extended or adjusted under 35 U.S.C. 154(b) by 0 days.

(21) Appl. No.: 19/536,031

(22) Filed: Feb. 10, 2026

(30) Foreign Application Priority Data

Jul. 15, 2025 (QZ) ..... PBR 2025/1575

(51) Int. Cl.
*A01H 5/00* (2018.01)
*A01H 6/00* (2018.01)

(52) U.S. Cl.
USPC ..... Plt./379
CPC ..... *A01H 6/00* (2018.05)

(58) Field of Classification Search
USPC ..... Plt./379
CPC ..... A01H 5/00
See application file for complete search history.

*Primary Examiner* — Kent L Bell
(74) *Attorney, Agent, or Firm* — James R. Holm; Plant Novelty Rights, LLC

(57) ABSTRACT

A new and distinct *Nephrolepis exaltata* plant named 'DEBO2025' particularly distinguished by uniquely curled foliage with each pinnae displaying a moderate to strong curling pattern giving the frond an overall ruffled appearance, compact, upright plant habit with a dense and bushy appearance due to its uniquely curled foliage, and darker green colored foliage compared to other *Nephrolepis exaltata* varieties known to the Inventor.

3 Drawing Sheets

Figure 1:
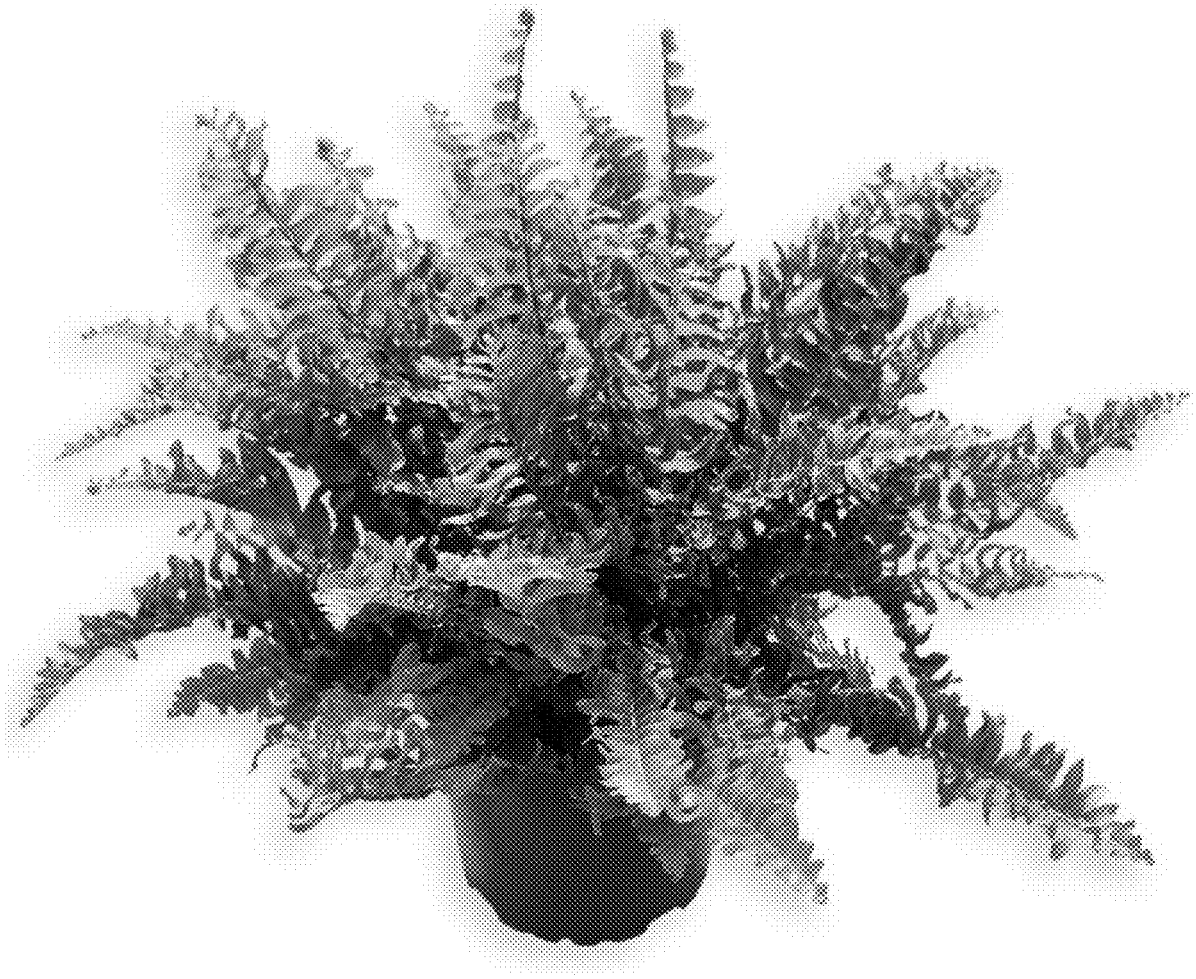

Genus and species: *Nephrolepis exaltata.*
Variety denomination: 'DEBO2025'.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period prior to the filing date. This application claims priority to CPVO application no. 2025/1575 filed on Jul. 15, 2025, which is herein incorporated by reference.

BACKGROUND OF THE NEW PLANT

The present invention comprises a new and distinct variety of *Nephrolepis exaltata*, and hereinafter referred to by the variety name 'DEBO2025'.

This new variety was discovered by the inventor as a naturally occurring shoot mutation of the *Nephrolepis exaltata* plant named 'Green Moment' (U.S. Plant Pat. No. 25,311). The discovery of the new variety was made by the inventor in July 2021 in a non-publicly accessible area of a commercial greenhouse located in Asten, the Netherlands. 'DEBO2025' was selected by the inventor due to its uniquely curled foliage with each pinnae displaying a moderate to strong curling pattern giving the frond an overall ruffled appearance.

Asexual reproduction of the new variety 'DEBO2025' was first performed in August 2021 via tissue culture in a laboratory located in Burgh-haamstede, the Netherlands. Access to all plants was restricted, as plants were kept in restricted locations that are not open to the public. Through subsequent propagation by tissue culture, multiple generations have been reproduced, which have shown that the unique features of 'DEBO2025' are stable and reproduced true to type.

SUMMARY OF THE INVENTION

The new variety 'DEBO2025' has not been observed under all possible environmental conditions. The phenotype may vary somewhat with variations in environment such as temperature, day length, light intensity, water status, fertilizer rate and type, without, however, any variance in genotype.

The following are the most outstanding and distinguishing characteristics of this new *Nephrolepis exaltata* variety. The combination of these characteristics distinguishes 'DEBO2025' as a new and distinct variety of *Nephrolepis exaltata:*

1. Uniquely curled foliage with each pinnae displaying a moderate to strong curling pattern giving the frond an overall ruffled appearance.
2. Compact, upright plant habit with a dense and bushy appearance due to its uniquely curled foliage.
3. Darker green colored foliage compared to other *Nephrolepis exaltata* varieties known to the Inventor.

DESCRIPTION OF THE PHOTOGRAPHS

This new *Nephrolepis exaltata* variety is illustrated by the accompanying colored photographs which show the overall appearance and distinct characteristics of the plant. The colors shown are as true as can be reasonably obtained by conventional photographic procedures. Colors in the photographs may differ slightly from the color values cited in the botanical description which accurately describe the colors of the new variety.

FIG. 1. Shows a side view of the overall plant form and foliage of 'DEBO2025'.

Figure 2:
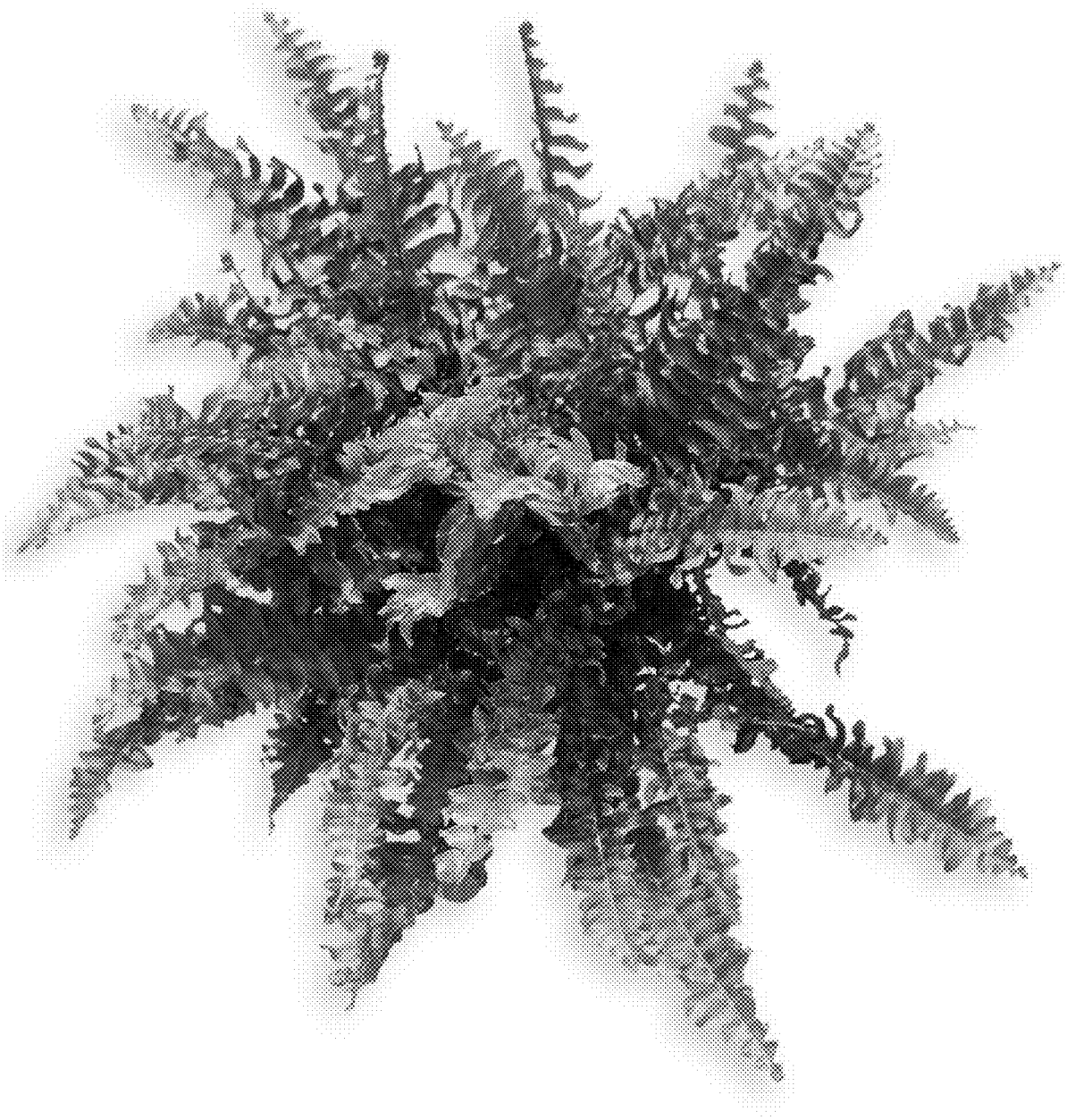

FIG. 2. Shows an overhead view of the overall plant form and foliage of 'DEBO2025'.

Figure 3:
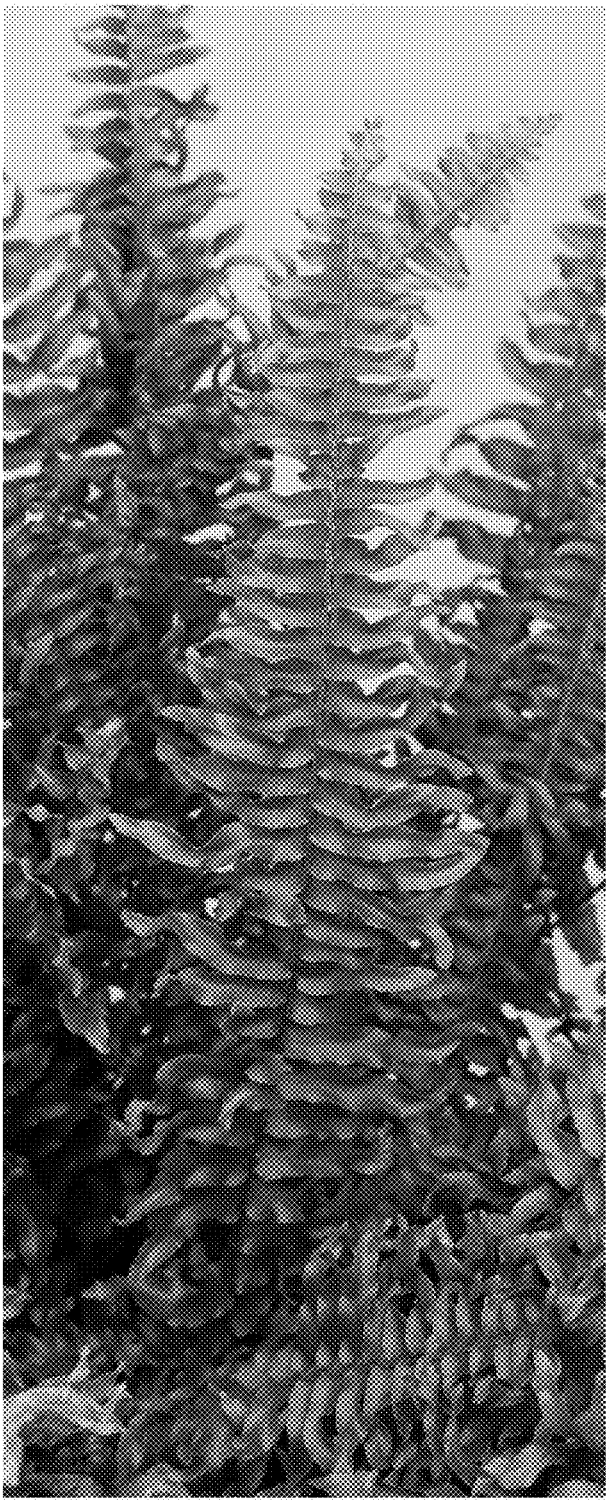

FIG. 3. Shows a close-up of a typical frond of 'DEBO2025'.

DESCRIPTION OF THE NEW VARIETY

In the following description, color references are made to The Royal Horticultural Society Colour Chart, Sixth Edition, except where general color terms of ordinary dictionary significance are used. The following observations and measurements describe plants grown in a greenhouse located in Asten, the Netherlands. Daytime greenhouse temperatures ranged from 20 to 24 degrees Celsius and nighttime greenhouse temperatures ranged from 16 to 18 degrees Celsius. Greenhouse light levels ranged between 8,000 and 15,000 LUX (750 to 1,400 footcandles). No artificial light, photoperiodic treatments were given to the plants. No chemical treatments were given to plants. Detailed descriptions and photographs were taken in August 2025 from 18-month-old plants grown in 19-centimeter containers. Measurements and numerical values represent averages of typical plants of 'DEBO2025'.

DETAILED BOTANICAL DESCRIPTION

Classification:

*Family*.—Nephrolepidaceae.

*Botanical*.—*Nephrolepis exaltata*.

*Common*.—*Nephrolepis*.

*Denomination*.—'DEBO2025'.

General description:

*Plant type*.—Herbaceous tropical perennial fern for use as a potted ornamental plant.

*Propagation type*.—Asexual propagation through tissue culture.

*Crop time*.—Approximately 22 weeks from a tissue-cultured plantlet to a finished plant in a 15-centimeter container.

*Plant habit*.—Compact, dense, and upright-arching fronds forming a full, symmetrical plant.

*Plant height from soil level to top of foliar plane*.—Approximately 37.2 cm.

*Plant width or area of spread*.—Approximately 71.7 cm.

*Growth rate*.—Moderate to high, forming a dense canopy quickly.

*Plant vigor*.—High.

*Branching characteristics*.—No branches present, fronds grow directly from the base of the plant.

*Roots*.—From the base of the plant, an average of 28 thin aerial roots grow beneath the foliar plane. Average length: 38.1 cm (longest measures 51.2 cm). Average diameter: 0.1 cm. Color: Mature roots are colored a blend of 152A (yellow-green) and N199A (greyed-brown); immature roots are colored 144A (yellow-green). Texture and luster: Glossy and sparsely covered with scaly hairs with an average length of 0.2 cm and colored a transparent 156D (greyed-white).

Foliage description:

*Frond*.—Type and arrangement: Compound pinnate and alternate. Number of fronds per plant: Approximately 130. Frond shape: Narrow elliptic to slightly twisted and rotated. Frond apex: Acute. Frond base: Straight to shallow truncate. Frond length: Average 45 to 55 cm. Frond width: Average 9.0 cm. Frond margin: Irregular finely dentate to serrate.

*Pinnae*.—Number of pinnae per frond: Average 62 (varying between 50 and 98). Pinnae shape: Broadly lanceolate, slightly carinate and slightly to moderately twisted and curled. Pinnae apex: Rounded to slightly reflexed. Pinnae length: Average 4.9 cm. Pinnae width: Average 1.3 cm. Pinnae margin: Moderately to strongly undulate.

*Texture and luster*.—Glabrous; upper side slightly glossy and underside very slightly glossy.

*Pubescence*.—Not present.

*Venation*.—Type: Pinnate. Color: Adaxial surface: 203A (black). Abaxial surface: A blend of 200A (brown) and 203A (black).

*Color*.—Immature foliage: Adaxial surface: 144A (yellow-green). Abaxial surface: 144A and 144B (yellow-green). Mature foliage: Adaxial surface: 143A (green). Abaxial surface: 137B (green).

*Rachis and stipe*.—Length: Average 39.1 cm; average stipe length is 7.9 cm. Width: Average 0.2 cm. Color: Upper side: 146A (yellow-green). Underside: A blend of 152A to 152C (yellow-green) and 200A to 200C (brown). Texture: Moderately covered with tufts of short scaly hairs having an average length of 0.5 mm and colored 156D (greyed-white).

Spore production: None observed.

Temperature tolerance: Indoor fern, hardy to at least USDA Zone 10 and temperatures up to 35 degrees Celsius.

Disease and pest tolerance: No claims are made to any superior disease or insect resistance or tolerance.

COMPARISON WITH PARENT VARIETY

The new *Nephrolepis exaltata* variety 'DEBO2025' can be distinguished from its parent variety 'Green Moment' (U.S. Plant Pat. No. 25,311) in the following characteristics described in Table 1 below.

TABLE 1

| Characteristic | 'DEBO2025' | 'Green Moment' |
|---|---|---|
| Plant habit. | Compact, symmetrical with upright-arching fronds forming a dense mound. | More open and spreading habit with less uniform frond distribution. |
| Frond length. | Medium to long, averaging 45-55 cm. | Typically longer, 55-65 cm. |
| Frond width. | Broad and uniform along length. | Slightly narrower toward the apex. |
| Frond curvature. | Arching to semi-pendant. | Predominantly pendant. |
| Color (upper surface). | Green (RHS 143A). | Medium green (approx. RHS 138A). |
| Color (lower surface). | Yellow green (RHS 137B). | Medium-light green (RHS 138C). |
| Rachis color. | Yellow-green with faint bronze tint on | Green without bronze hue. |

TABLE 1-continued

| Characteristic | 'DEBO2025' | 'Green Moment' |
|---|---|---|
| | young fronds. | |
| Pinnae shape. | Broadly lanceolate, slightly carinate and slightly to moderately twisted and curled. | Narrower, more linear pinnae with flat margins. |
| Pinnae spacing. | Close to overlapping. | Moderately spaced. |
| Pinnae apex. | Rounded and slightly reflexed. | Acute to flat. |
| Growth rate. | Moderate to high, forming a dense canopy quickly. | Slightly faster with looser growth |
| Overall appearance. | Compact, dense and symmetrical. | Larger, less symmetrical with looser foliage growth. |

COMPARISON WITH COMMERCIAL VARIETY

The new *Nephrolepis exaltata* variety 'DEBO2025' can be distinguished from the related known variety of *Nephrolepis exaltata* 'Green Lady' (unpatented) in the following characteristics described in Table 2 below.

TABLE 2

| Characteristic | 'DEBO2025' | 'Green Lady' |
|---|---|---|
| Plant habit. | Compact, symmetrical with upright-arching fronds forming a dense mound. | More spreading and open with arching to semi-pendant fronds. |

TABLE 2-continued

| Characteristic | 'DEBO2025' | 'Green Lady' |
|---|---|---|
| Overall size. | Slightly smaller. | Slightly larger. |
| Frond length. | 45-55 cm. | 55-65 cm. |
| Frond width. | Broader and fuller, maintaining consistent width. | Narrower with tapered apex. |
| Frond curvature. | Arching to semi-pendant. | Predominantly pendant. |
| Color (upper surface). | Green (RHS 143A). | Medium green (RHS 138A). |
| Color (lower surface). | Yellow-green (RHS 137B). | Medium-light green (RHS 138C) |
| Rachis color. | Medium green with faint bronze tint on young fronds. | Uniformly medium green. |
| Pinnae shape. | Broadly lanceolate, slightly carinate and slightly to moderately twisted and curled. | Narrower, more linear and flat. |
| Pinnae spacing. | Close to overlapping. | Moderately spaced. |
| Pinnae apex. | Rounded and slightly reflexed. | Acute to narrowly rounded. |
| Growth rate. | Moderate to high, forming a dense canopy quickly. | Faster and more open habit. |
| Overall appearance. | Compact, dense and symmetrical. | Larger, more arching, and less dense. |

What is claimed is:

1. A new and distinct variety of *Nephrolepis exaltata* plant named 'DEBO2025', substantially as illustrated and described herein.

* * * * *